(12) United States Patent
Crescimanno

(10) Patent No.: US 9,603,786 B1
(45) Date of Patent: Mar. 28, 2017

(54) LOW HAZE FILM FORMERS FOR TOP COAT NAIL POLISH

(71) Applicant: MYCONE DENTAL SUPPLY CO., INC., Gibbstown, NJ (US)

(72) Inventor: Stephen Crescimanno, Hatfield, PA (US)

(73) Assignee: Mycone Dental Supply Co., Inc., Gibbstown, NJ (US)

( * ) Notice: Subject to any disclaimer, the term of this patent is extended or adjusted under 35 U.S.C. 154(b) by 0 days.

(21) Appl. No.: 15/004,432

(22) Filed: Jan. 22, 2016

(51) Int. Cl.
*A61K 8/81* (2006.01)
*A61Q 3/02* (2006.01)
*A61K 8/73* (2006.01)
*C08F 220/14* (2006.01)

(52) U.S. Cl.
CPC ............ *A61K 8/8152* (2013.01); *A61K 8/731* (2013.01); *A61Q 3/02* (2013.01); *C08F 220/14* (2013.01); *A61K 2800/262* (2013.01); *A61K 2800/594* (2013.01); *A61K 2800/95* (2013.01)

(58) Field of Classification Search
None
See application file for complete search history.

(56) References Cited

U.S. PATENT DOCUMENTS

| | | | |
|---|---|---|---|
| 3,971,708 A | 7/1976 | Davis | |
| 4,421,881 A | 12/1983 | Benkendorf et al. | |
| 5,356,616 A | 10/1994 | Sojka | |
| 5,639,447 A | 6/1997 | Patel | |
| 5,785,958 A | 7/1998 | Sirdesai | |
| 6,051,242 A | 4/2000 | Patel | |
| 6,352,687 B1 | 3/2002 | Ismailer | |
| 6,982,076 B2 | 1/2006 | Kaneko et al. | |
| 2007/0189995 A1 | 8/2007 | Weber | |
| 2013/0149266 A1 | 6/2013 | Homma et al. | |
| 2015/0297486 A1 | 10/2015 | Kergosien et al. | |
| 2015/0306013 A1 | 10/2015 | Kergosien et al. | |
| 2015/0313826 A1 | 11/2015 | Kergosien | |
| 2015/0328104 A1 | 11/2015 | Kergosien | |

FOREIGN PATENT DOCUMENTS

| | | | | |
|---|---|---|---|---|
| JP | H6-279239 | * | 10/1994 | ........... A61K 8/8152 |
| JP | H6-279239 A | | 10/1994 | |
| JP | 2001-114650 | * | 4/2001 | ........... A61K 8/8152 |

\* cited by examiner

*Primary Examiner* — Brian Gulledge
(74) *Attorney, Agent, or Firm* — Peter D. Mlynek; Law Offices of Peter D. Mlynek

(57) ABSTRACT

A top coat nail polish formulation comprising a primary film-forming polymer, a secondary film-forming polymer, a plasticizer and a solvent yields a haze free film upon drying. The secondary film-forming polymer is prepared by a reaction methacrylic acid, alkylacrylate, and of methyl methacrylate, at selected ratios. The alkylacrylate comprises a branched alkyl group with 4 to 12 carbons, or a mixture of branched alkyl groups and optionally linear alkyl group. The haze of the dried top coat film depends on the presence of methacrylic acid, ratio of alkylacrylate to methyl methacrylate, the number of carbons in the alkyl group on the alkylacrylate, and the branching of the alkyl group.

10 Claims, No Drawings

LOW HAZE FILM FORMERS FOR TOP COAT NAIL POLISH

FIELD OF THE INVENTION

The present invention is directed to an acrylate/methacrylate copolymer for use in preparation of a top coat nail polish formulation, to the top coat nail polish formulation, and a solution comprising the copolymer. The top coat nail polish formulation comprising the copolymer yields a hardened nail polish that is haze-free.

DESCRIPTION OF RELATED TECHNOLOGY

Numerous types of top coat nail polish formulations are commercially available. Top coat nail polish formulations typically contain a primary film former such as nitrocellulose, a secondary film former, a plasticizer, and one or more solvents such alcohols and acetates.

There are a number of desirable properties which top coat nail polish formulation polish should possess, such as low drying time, strong adherence of the dried film to the nail substrate, wear resistivity, elasticity, and be dermatologically safe. In addition, top coat nail polish formulations should exhibit ease in application of the formulation onto the nail substrate, good shelf stability, resistivity to separation or sedimentation of its components.

A set of important properties of a dried top coat film are the esthetic characteristics that it provides to the end user. Preparing formulations that fulfill the practical and technical considerations, including those listed above, but additionally serve the ever-changing esthetic demands of the end user, require increasingly complicated formulations.

One such sought after esthetic characteristic is the lack of haze in formed dried top coat films. The mechanics that cause the formation of haze or milky appearance is not well understood, but it is hypothesized that the haze is due to microstructures in the dried nail polish films. The formation of such microstructure varies widely with the formulation components, loading levels of such components, process parameters, and other formulatory parameters. A thorough theoretical investigation of the causes of the formation of microstructures is elusive, and a systematic empirical investigation of this phenomenon is difficult because of the many competing parameters due to the complex formulations of top coat nail polish formulations.

Mitigation of haze in a transparent nail polish both wet and dry that comprised light reflecting decorative materials is taught in U.S. Pat. No. 6,352,687. The technique disclosed included the addition of suspending agents to the formulation. The suspending agents consisting essentially of fumed silica.

Nail polishes comprising a nitrocellulose primary film former and, an acrylic secondary film former are well known in the nail polish formulation arts. For example, nitrocellulose lacquer composition containing gelatin and acrylic copolymers are described in U.S. Pat. No. 4,421,881. Nitrocellulose-based lacquer compositions are suitable for application as surface coatings for human nails. The lacquers are comprised on an overall basis of a primary film former which is nitrocellulose, two or more film formers, one of which is always acrylic copolymer present in proportion of at least about 10% and no more than about 70% by weight of the total secondary film formers specified, water-soluble animal gelatin, suitable plasticizers and liquid carriers therefor, including solvents, couplers and diluents, all of which liquid carriers are for the most part evaporants. Such compositions are free-flowing liquids which provide tough coatings when they harden, being firmly adhering, durable coatings which remain intact for periods of time of at least 3-6 days under a variety of conditions in the everyday environment. The cured coatings have a "wet look" of freshly applied lacquer which is retained for extended periods.

Quick drying compositions, including several compositions comprising nitrocellulose and methacrylates, are disclosed in U.S. Pat. Nos. 5,639,447 and 6,051,242. The quick drying composition for application to nails comprises a base or lacquer component and an optional pigment component. The base component can dry in less than about 70 seconds under ambient conditions, yet is free of undesirable solvents and components such as acetone, toluene, chlorinated hydrocarbons, and formaldehyde-containing resins. The base component includes film-forming polymers, a monomer component compatible with the polymers, and a free radical source.

To improve the wear resistance of nail polish comprising acrylic polymers, changes to the structure of the acrylic polymer may be made. For example, U.S. Pat. No. 5,356,616, discloses a film forming resin which is a blend of: (i) a graft copolymer having a main backbone chain of acrylic ester units and methacrylic ester units, with the main backbone chain having grafted thereto pendant trialkoxysilyl groups and pendant ethylene glycol dimethacrylate groups, and (ii) a silsesquioxane resin containing $RSiO_{3/2}$ units and $\equiv$SiOH units in which R is an alkyl group or an aryl group. There is a further disclosure of graft copolymer containing, pendant trialkoxysilyl groups, and pendant vinylbenzyl chloride groups.

Non-yellowing rapid drying nail polish top-coat compositions comprising a primary film-forming polymer and a methacrylate were disclosed in U.S. Pat. No. 5,785,958. The rapid-drying, durable coating composition for formation of a durable top coat with a glossy look, is comprised of a base resin of cellulose acetate butyrate and an aliphatic ester monomer. Additional components include a film former, a cross-linking agent, an inhibitor to polymerization and a solvent.

Several colored nail polish formulations comprising nitrocellulose, acrylates copolymer and phthalic anhydride are disclosed in U.S. Patent Application Publication No. 2007/0189995. This patent publication teaches a process for making a cosmetic nail composition comprising several viscosity defined gelled nail polish components including a gelling agent, a film former, a solvent and a colorant, and combining the same with a chemical viscosity reducing agent to form a custom-colored nail polish varnish having of a certain viscosity.

Japanese Patent Laid-Open Publication No. H6-279239 discloses a nail-care composition using as a film-forming agent, a copolymer having a molecular weight of 10,000-70,000 comprised of 20-85% by weight 45 of styrene and/or methyl methacrylate, 5-60% by weight of an alkyl acrylate ester (the alkyl chain length of 1-8), and 7-30% by weight of acrylic acid.

A nail enamel comprising nitrocellulose, and a methyl methacrylate/butyl methacrylate/2-ethylhexyl methacrylate copolymer with a weight average molecular weight of 8,000 g/mol, is disclosed in U.S. Pat. No. 6,982,076. That patent provides a solvent-based nail-care composition which can be easily applied to nails, provides a film (coating film) on the nail with excellent strength and gloss, and generates a coating film that is difficult to peel off over time and free from loss of gloss. Such a composition comprises nitrocellulose; neopentyl glycol trimellitate adipate polyester resin; one, two, or more members selected from the group consisting of alkyl methacrylate-alkyl acrylate copolymers, sucrose benzoate, and a polymer compound having a glass transition temperature of 50° C. to 80° C., and a solvent.

Copolymers having carboxylic acid groups such as butyl acrylate-methyl methacrylate-methacrylic acid copolymers, and vinyl acetate-acrylic acid copolymers are exemplified in U.S. Pat. No. 3,971,708 as anionic resins for film forming at the electrodeposition bath temperature and are heat curable with the aminoplast or phenoplast resin to yield a tack-free film. Controlled paint film flow during curing of the film at elevated temperature for avoidance of inadequately coated areas is obtained in an electrocoating operation of an electrode workpiece employing as paint vehicle a mixture of electrodepositable resin and water-dispersible aminoplast or phenoplast resin crosslinkable therewith by incorporating into said vehicle, or into the bath containing same, a small proportion of curing accelerator acid such as a sulfonic acid which is codepositable with said paint film in concentration sufficient for yielding a substantially continuous cured film on the resulting coated substrate.

Quick drying nail polish composition comprising nitrocellulose or cellulose acetate butyrate polymer with methyl/lauryl methacrylate copolymer dissolved in organic solvents (Elvacite 2552C) is disclosed in U.S. Patent Application Publication No. 2013/0149266. The lacquer component can harden in ambient atmosphere without the use of ultraviolet radiation to provide a long lasting nail polish film.

Although many advances in the art of formulating nail polish compositions have been made to solve many problems, such as lowering drying time, improving wearability, obviating health concerns, overcoming esthetic concerns remain. A need continues for top coat nail polish formulations, which form a dry top coat film that exhibits a low degree of haze.

SUMMARY OF THE INVENTION

The present invention relates to a copolymer of methyl methacrylate, methacrylic acid and an alkylacrylate, suitable for use in a top coat nail polish formulation.

One type of a copolymer of the present invention is prepared by a reaction of: (a) about 0.5 wt % to about 5 wt % of methacrylic acid; (b) about 25 wt % to about 45 wt % of at least one alkylacrylate, wherein alkylacrylate is $CH_2=CH-C(O)-OR$, wherein R is a branched $C_4$ to $C_{12}$ alkyl group; and (c) about 50 to about 74.5 wt % of methyl methacrylate. This copolymer may be prepared by adding a mixture of methacrylic acid, alkyl acrylate and methyl methacrylate to a stirred solution of a solvent. At least one free radical polymerization initiator may be added to polymerization reaction. The ratio of the three monomers is selected to reflect the desired weight ratios of the units in the copolymer.

The copolymerization of methacrylic acid, alkyl acrylate and methyl methacrylate generally occurs at elevated temperatures, such as between 50° C. and 150° C. The length of the reaction time needed for the synthesis of the copolymer to completion depends on various factors, and may be between 1 minute and 12 hours. The copolymerization of methacrylic acid, alkyl acrylate and methyl methacrylate is a free radical polymerization that needs to be carried out under inert atmosphere such as nitrogen.

Suitable solvents for solution polymerizations include methyl acetate, ethyl acetate, isopropyl acetate, methyl ethyl ketone, acetone, methanol, ethanol, n-propanol, isopropanol, n-butanol, and mixtures thereof. The amount of solvent is generally about 30 to about 80 percent by weight based on the total weight of the reactants and solvent.

The reactants used to prepare the copolymer are methyl methacrylate monomer, methacrylic acid monomer and alkylacrylate monomer. Suitable alkylacrylates for the preparation of the copolymer of the present invention have the structural formula $CH_2=CH-C(O)-OR$, wherein R is a branched $C_4$ to $C_{12}$ alkyl group. The alkylacrylate may be a mixture of different alkylacrylates, and thus the alkylacrylate in the copolymer may contain a mixture of alkyl groups. Under one embodiment the branched alkyl group is selected from the group consisting of iso-butyl, tert-butyl, 2-methylbutyl, 5-methylhexyl, 2-ethylhexyl, iso-octyl, 6-methylheptyl, 3,5,5-trimethylhexyl, 8-methylnonyl, and iso-decyl. Under another embodiment the branched alkyl group 2-ethylhexyl.

Another type of copolymer of the present invention is prepared by a reaction of (a) about 0.5 to about 5 wt % of methacrylic acid; (b) about 25 to about 45 wt % of a mixture of at least one branched $C_4$ to $C_1$ alkyl acrylate and zero, one or more linear $C_3$ to $C_{16}$ alkyl acrylate; and (c) about 50 to about 74.5 wt % of methyl methacrylate. This copolymer comprises acrylate units that comprise one or more branched alkyl groups, and optionally one or more linear alkyl groups. In this type of a copolymer of the present invention, the mixture of alkyl groups may be a mixture of branched alkyl groups, or a mixture of linear and branched alkyl groups.

To assist the polymerization of the methacrylic acid, alkyl acrylate, and methyl methacrylate monomers to form the copolymer of the present invention and in order to regulate the molecular weight of copolymer, a chain transfer agent may be added. Further, the polymerization of the monomers in the reaction mixture is undertaken in the presence of 0.001 to 1 wt % of one or more initiators.

At the completion of the reaction, it is desirable to have the residual levels of any or all of the monomers to be less than 0.1 wt %, by performing an optional step of adding an initiator chase.

After the completion of the reaction, including the optional initiator chase step, the mixture may be cooled and transferred to a storage vessel, or used further in the preparation of the nail polish top coat composition. The copolymer of the present invention is typically not isolated from solvent, and is used as a solution in any further preparation of the top coat nail polish formulation.

The present invention is also directed to a solution comprising the copolymer described above. This solution for use in the preparation of a top coat nail polish formulation comprises (1) the copolymer prepared by a reaction of: (a) about 0.5 wt % to about 5 wt % of methacrylic acid; (b) about 25 wt % to about 45 wt % of at least one alkylacrylate of formula $CH_2=CH-C(O)-OR$, wherein R is a branched $C_4$ to $C_{12}$ alkyl group; and (c) about 50 wt % to about 74.5 wt % of methyl methacrylate; and (2) a solvent selected from the group consisting of methyl acetate, ethyl acetate, isopropyl acetate, methyl ethyl ketone, methanol, ethanol, n-propanol, isopropanol, n-butanol, and mixtures thereof.

The present invention is also directed to a top coat nail polish composition comprising a top coat component that is useful in the manicure and pedicure arts. The top coat component comprises: (a) about 5 wt % to about 30 wt % primary film-forming polymer comprises at least one polymer selected from the group consisting of cellulose acetate, cellulose acetate butyrate, cellulose acetate propionate, ethyl cellulose, vinyl polymers, nitrocellulose, and mixtures thereof; (b) about 2 wt % to about 20 wt % secondary film-forming polymer; (c) about 1 wt % to about 5 wt % of at least one plasticizer; and (d) about 50 wt % to about 80 wt % solvent; said wt % of components (a) to (d) are based on the total weight of the component; and wherein the secondary film-forming polymer comprises the copolymer prepared by a reaction of: (i) about 0.5 to about 5 wt % of methacrylic acid; (ii) about 25 to about 45 wt % of $CH_2=CH-C(O)-OR$, wherein R is a branched $C_4$ to $C_{12}$ alkyl group; and (iii) about 50 to about 74.5 wt % of methyl methacrylate; said wt % of components (i) to (iii) are based on the total weight of the copolymer.

One of the advantage of the present formulation over prior art is the reduction of haze in a typical nail polish formulation. There appear to be four factors associated with the copolymer composition that govern the haze characteristics in the typical dried nail formulations comprising the copolymer.

The first factor is the presence of methacrylic acid. Methacrylic acid monomer is necessary in the preparation of the copolymer of the present invention.

The second factor is the weight ratio of methyl methacrylate to alkyl acrylate. The haze is reduced or eliminated when the weight ratio of alkyl acrylate to methyl methacrylate is between about 1:1 and 1:3. A strong haze is present if the majority of the polymer is alkyl acrylate or there is too little of the alky acrylate. In order to eliminate or minimize haze, judicious selection of the weight percentages is generally required. The weight percentages of the methacrylic acid, alkyl acrylate, and methyl methacrylate is about 1 wt % to about 2 wt %:about 29 wt % to about 33 wt %:about 65 wt % to about 70 wt %.; or about 1 wt % to about 2 wt %:about 33 wt % to about 37 wt %:about 61 wt % to about 66 wt %; or about 1 wt % to about 2 wt %:about 37 wt % to about 41 wt %:about 57 to about 62 wt %.

The third factor associated with the copolymer composition that determines the haze characteristics in the typical dried nail formulations comprising the copolymer is the number of carbon atoms in the alkyl group in the alkyl acrylate. The average number of carbons in the alkyl group in alkylacrylate is 4 to 12 or 4 to 10. The alkylacrylate may be a single species, or a mixture of two or more compounds each of which is also an alkylacrylate.

The fourth factor is the branching of the alkyl group of the alkylacrylate. The alkylacrylate may be a mixture of different alkylacrylates, and thus the alkylacrylate in the copolymer may contain a mixture of alkyl groups. This mixture of alkyl groups may be a mixture of branched alkyl groups, or a mixture of linear and branched alkyl groups.

The reaction of ingredients (a) primary film-forming polymer, (b) secondary film component, (c) plasticizer, and (d) solvent, as described above, form a top coat component for use in preparing a top coat nail polish composition. One of the advantages of the top coat formed by the application of the clear nail polish composition of the present invention is the lack of or low amounts of haze.

The top coat nail polish formulation is a lacquer that may be applied to fingernails or toenails. Of a particular use of the top coat nail polish composition of the present invention is the formation of the final layer of a manicure. The top coat nail polish formulation is applied after applying a colored nail polish. When applied and dried, the top coat forms a hardened barrier for the nail which gives nails a glossy shine, prevents chipping and scratching of the colored layer. One of the advantages of the top coat formed by the application of the clear nail polish composition of the present invention is the lack of or low amounts of haze. The top coat nail formulation can also be used in applications outside of the manicure and pedicure arts.

The amounts of primary film-forming polymer and secondary film-forming polymer are selected to produce a dried coating thickness of about 0.001 inches to about 0.005 inches (about 25 m to 125 μm), preferably about 0.002 inches to 0.003 inches (50 μm to 75 μm).

The primary film-forming polymers provide body and viscosity functionality in the top coat nail polish composition. Primary film-formers useful in the top coat component are selected for their hardness, toughness, resistance to abrasion and ability to release solvent rapidly. Primary film-forming polymers useful in the top coat component include cellulose acetate, cellulose acetate propionate, cellulose acetate butyrate, ethyl cellulose, vinyl polymers, nitrocellulose, and mixtures thereof.

The secondary film-forming component in the top coat composition necessarily comprises the copolymer of the present application described above. Additional secondary film formers useful in the base component include drying and nondrying alkyd resin, vinyl polymers such as polyvinyl acetate and polyvinyl butyral; arylsulfonamide-formaldehyde resins, for example toluene sulfonamide-formaldehyde resin, polyether urethanes such as polyurethane resins; polyester resins from mixtures of 2,2,4-trimethyl-1,3-pentanediol, isophthalic acid-85, and trimellitic anhydride.

Plasticizers employed in the top coat composition are chosen to impart flexibility to the hardened coating. Commonly used plasticizers are from the chemical classes of sebacates, adipates, terephthalates, dibenzoates, phthalates, azelates, glycols, polyethers and polycarboxylic acids with linear or branched aliphatic alcohols and blends of these. These compounds are selected on the basis of low toxicity, compatibility with the nail plate, formula composition and with the final polymerized material. The plasticizer is employed in the top coat composition in an amount of about 1 wt % to about 5 wt %. Alternatively, the plasticizer is employed in the top coat composition in an amount of about 1 wt % to about 3 wt %.

Suitable solvents for use in preparation of the top coat composition include alkanes having 4 to 10 carbon atoms per molecule, aliphatic esters having 3 to 10 carbon atoms per molecule, alkanols having 2 to 10 carbon atoms per molecule. Suitable solvents may be selected from the group consisting of methyl acetate, ethyl acetate, isopropyl acetate, methyl ethyl ketone, acetone, methanol, ethanol, n-propanol, isopropanol, n-butanol, and mixtures thereof. The amount of solvent is generally about 50 to about 85 percent by weight based on the total weight of the top coat composition.

The invention is defined by at least fifteen aspects.

In a first aspect, the present invention relates to a copolymer prepared by a reaction of about 0.5 wt % to about 5 wt % of methacrylic acid; about 25 wt % to about 45 wt % of at least one alkylacrylate of formula $CH_2=CH-C(O)-OR$, wherein R is a branched $C_4$ to $C_{12}$ alkyl group; and about 50 wt % to about 74.5 wt % of methyl methacrylate.

In a second aspect, the present invention relates to a copolymer prepared by a reaction of about 1 wt % to about 2 wt % of methacrylic acid; about 29 wt % to about 33 wt % of at least one alkylacrylate of formula $CH_2=CH-C(O)-OR$, wherein R is a branched $C_6$ to $C_{10}$ alkyl group; and about 65 wt % to about 70 wt % of methyl methacrylate.

In a third aspect, the present invention relates to a copolymer prepared by a reaction of about 1 wt % to about 2 wt % of methacrylic acid; about 33 wt % to about 37 wt % of at least one alkylacrylate of formula $CH_2=CH-C$ (O)—OR, wherein R is a branched $C_6$ to $C_{10}$ alkyl group; and about 61 wt % to about 66 wt % of methyl methacrylate.

In a fourth aspect, the present invention relates to a copolymer prepared by a reaction of about 1 wt % to about 2 wt % of methacrylic acid; about 37 wt % to about 41 wt % of at least one alkylacrylate of formula $CH_2$=CH—C(O)—OR, wherein R is a branched $C_6$ to $C_{10}$ alkyl group; and about 57 wt % to about 62 wt % of methyl methacrylate.

In a fifth aspect, the present invention relates to a copolymer prepared by a reaction of about 0.5 wt % to about 5 wt % of methacrylic acid; about 25 wt % to about 45 wt % of at least one alkylacrylate of formula $CH_2$=CH—C(O)—OR, wherein R is selected from the group consisting of iso-butyl, tert-butyl, 2-methylbutyl, 5-methylhexyl, 2-ethylhexyl, iso-octyl, 6-methylheptyl, 3,5,5-trimethylhexyl, 8-methylnonyl, and iso-decyl; and about 50 wt % to about 74.5 wt % of methyl methacrylate.

In a sixth aspect, the present invention relates to a copolymer prepared by a reaction of about 0.5 wt % to about 5 wt % of methacrylic acid; about 25 wt % to about 45 wt % of at least one alkylacrylate of formula $CH_2$=CH—C(O)—OR, wherein R is 2-ethylhexyl; and about 50 wt % to about 74.5 wt % of methyl methacrylate.

In a seventh aspect, the present invention relates to a copolymer prepared by a reaction of about 0.5 wt % to about 5 wt % of methacrylic acid; about 25 wt % to about 45 wt % of at least one alkylacrylate of formula $CH_2$=CH—C(O)—OR, wherein R is a branched $C_4$ to $C_{12}$ alkyl group; about 50 wt % to about 74.5 wt % of methyl methacrylate; and up to about 15 wt % of at least one alkylacrylate of formula $CH_2$=CH—C(O)—OR, wherein R is a linear chain $C_3$ to $C_{16}$ alkyl group.

In an eighth aspect, the present invention relates to a top coat nail polish formulation comprising a top coat composition comprising: (a) about 5 wt % to about 30 wt % primary film-forming polymer comprises at least one polymer selected from the group consisting of cellulose acetate, cellulose acetate propionate, cellulose acetate butyrate, ethyl cellulose, vinyl polymers, nitrocellulose, and mixtures thereof; (b) about 2 wt % to about 20 wt % secondary film-forming polymer; (c) about 1 wt % to about 5 wt % of at least one plasticizer, and (d) about 50 wt % to about 85 wt % solvent; said wt % of components (a) to (d) are based on the total weight of the component; and wherein the secondary film-forming polymer comprises a copolymer prepared by a reaction of: (i) about 0.5 wt % to about 5 wt % of methacrylic acid; (ii) about 25 wt % to about 45 wt % of at least one alkylacrylate of formula $CH_2$=CH—C(O)—OR, wherein R is a branched $C_4$ to $C_{12}$ alkyl group; and (iii) about 50 wt % to about 74.5 wt % of methyl methacrylate; said wt % of components (i) to (iii) are based on the total weight of the copolymer.

In a ninth aspect, the present invention relates to a top coat nail polish formulation comprising a top coat composition comprising: (a) about 5 wt % to about 30 wt % primary film-forming polymer comprises at least one polymer selected from the group consisting of cellulose acetate, cellulose acetate propionate, cellulose acetate butyrate, ethyl cellulose, vinyl polymers, nitrocellulose, and mixtures thereof; (b) about 2 wt % to about 20 wt % secondary film-forming polymer: (c) about 1 wt % to about 5 wt % of at least one plasticizer; and (d) about 50 wt % to about 85 wt % solvent; said wt % of components (a) to (d) are based on the total weight of the component; and wherein the secondary film-forming polymer comprises a copolymer prepared by a reaction of: (i) about 1 wt % to about 2 wt % of methacrylic acid; (ii) about 29 wt % to about 33 wt % of at least one alkylacrylate of formula $CH_2$=CH—C(O)—OR, wherein R is a branched $C_4$ to $C_{12}$ alkyl group; and (iii) about 65 wt % to about 70 wt % of methyl methacrylate; said wt % of components (i) to (iii) are based on the total weight of the copolymer.

In a tenth aspect, the present invention relates to a top coat nail polish formulation comprising a top coat composition comprising: (a) about 5 wt % to about 30 wt % primary film-forming polymer comprises at least one polymer selected from the group consisting of cellulose acetate, cellulose acetate propionate, cellulose acetate butyrate, ethyl cellulose, vinyl polymers, nitrocellulose, and mixtures thereof; (b) about 2 wt % to about 20 wt % secondary film-forming polymer; (c) about 1 wt % to about 5 wt % of at least one plasticizer; and (d) about 50 wt % to about 85 wt % solvent; said wt % of components (a) to (d) are based on the total weight of the component; and wherein the secondary film-forming polymer comprises a copolymer prepared by a reaction of: (i) about 1 wt % to about 2 wt % of methacrylic acid; (ii) about 33 wt % to about 37 wt % of at least one alkylacrylate of formula $CH_2$=CH—C(O)—OR, wherein R is a branched $C_4$ to $C_{12}$ alkyl group; and (iii) about 61 wt % to about 66 wt % of methyl methacrylate; said wt % of components (i) to (iii) are based on the total weight of the copolymer.

In an eleventh aspect, the present invention relates to a top coat nail polish formulation comprising a top coat composition comprising: (a) about 5 wt % to about 30 wt % primary film-forming polymer comprises at least one polymer selected from the group consisting of cellulose acetate, cellulose acetate propionate, cellulose acetate butyrate, ethyl cellulose, vinyl polymers, nitrocellulose, and mixtures thereof; (b) about 2 wt % to about 20 wt % secondary film-forming polymer; (c) about 1 wt % to about 5 wt % of at least one plasticizer; and (d) about 50 wt % to about 85 wt % solvent; said wt % of components (a) to (d) are based on the total weight of the component; and wherein the secondary film-forming polymer comprises a copolymer prepared by a reaction of: (i) about 1 wt % to about 2 wt % of methacrylic acid; (ii) about 37 wt % to about 41 wt % of at least one alkylacrylate of formula $CH_2$=CH—C(O)—OR, wherein R is a branched $C_4$ to $C_{12}$ alkyl group; and (iii) about 57 wt % to about 62 wt % of methyl methacrylate; said wt % of components (i) to (iii) are based on the total weight of the copolymer.

In a twelfth aspect, the present invention relates to a top coat nail polish formulation comprising a top coat composition comprising: (a) about 5 wt % to about 30 wt % primary film-forming polymer comprises at least one polymer selected from the group consisting of cellulose acetate, cellulose acetate propionate, cellulose acetate butyrate, ethyl cellulose, vinyl polymers, nitrocellulose, and mixtures thereof; (b) about 2 wt % to about 20 wt % secondary film-forming polymer; (c) about 1 wt % to about 5 wt % of at least one plasticizer; and (d) about 50 wt % to about 85 wt % solvent; said wt % of components (a) to (d) are based on the total weight of the component; and wherein the secondary film-forming polymer comprises a copolymer prepared by a reaction of: (i) about 1 wt % to about 2 wt % of methacrylic acid; (ii) about 29 wt % to about 33 wt % of at least one alkylacrylate of formula $CH_2$=CH—C(O)—OR, wherein R is selected from the group consisting of iso-butyl, tert-butyl, 2-methylbutyl, 5-methylhexyl, 2-ethylhexyl, isooctyl, 6-methylheptyl, 3,5,5-trimethylhexyl, 8-methylnonyl, and isodecyl; and (iii) about 65 wt % to about 70 wt % of methyl methacrylate; said wt % of components (i) to (iii) are based on the total weight of the copolymer.

In a thirteenth aspect, the present invention relates to a top coat nail polish formulation comprising a top coat composition comprising: (a) about 5 wt % to about 30 wt % primary film-forming polymer comprises at least one polymer selected from the group consisting of cellulose acetate, cellulose acetate propionate, cellulose acetate butyrate, ethyl cellulose, vinyl polymers, nitrocellulose, and mixtures thereof; (b) about 2 wt % to about 20 wt % secondary film-forming polymer; (c) about 1 wt % to about 5 wt % of at least one plasticizer, and (d) about 50 wt % to about 85 wt % solvent; said wt % of components (a) to (d) are based on the total weight of the component; and wherein the secondary film-forming polymer comprises a copolymer prepared by a reaction of: (i) about 1 wt % to about 2 wt % of methacrylic acid; (ii) about 29 wt % to about 33 wt % of at least one alkylacrylate of formula $CH_2=CH-C(O)-OR$, wherein R is 2-ethylhexyl; and (iii) about 65 wt % to about 70 wt % of methyl methacrylate; said wt % of components (i) to (iii) are based on the total weight of the copolymer.

In a fourteenth aspect, the present invention relates to a top coat nail polish formulation comprising a top coat composition comprising: (a) about 5 wt % to about 30 wt % primary film-forming polymer comprises at least one polymer selected from the group consisting of cellulose acetate, cellulose acetate propionate, cellulose acetate butyrate, ethyl cellulose, vinyl polymers, nitrocellulose, and mixtures thereof; (b) about 2 wt % to about 20 wt % secondary film-forming polymer; (c) about 1 wt % to about 5 wt % of at least one plasticizer, and (d) about 50 wt % to about 85 wt % solvent; said wt % of components (a) to (d) are based on the total weight of the component; and wherein the secondary film-forming polymer comprises a copolymer prepared by a reaction of: (i) about 1 wt % to about 2 wt % of methacrylic acid; (ii) about 25 wt % to about 45 wt % of at least one alkylacrylate of formula $CH_2=CH-C(O)-OR$, wherein R is a branched $C_4$ to $C_{12}$ alkyl group, and optionally up to 15 wt % of at least one alkylacrylate of formula $CH_2=CH-C(O)-OR$, wherein R is a linear $C_3$ to $C_{16}$ alkyl group; and (iii) about 50 wt % to about 74.5 wt % of methyl methacrylate; said wt % of components (i) to (iii) are based on the total weight of the copolymer.

In a fifteenth aspect, the present invention relates to a solution suitable for use in the preparation of a top coat nail polish formulation, comprising a copolymer prepared by a reaction of about 0.5 wt % to about 5 wt % of methacrylic acid; about 25 wt % to about 45 wt % of at least one alkylacrylate of formula $CH_2=CH-C(O)-OR$, wherein R is a branched $C_4$ to $C_{12}$ alkyl group; and about 50 wt % to about 74.5 wt % of methyl methacrylate; and a solvent selected from the group consisting of methyl acetate, ethyl acetate, isopropyl acetate, methyl ethyl ketone, acetone, methanol, ethanol, n-propanol, isopropanol, n-butanol, and mixtures thereof.

DETAILED DESCRIPTION OF THE INVENTION

For illustrative purposes, the principles of the present invention are described by referencing various exemplary embodiments thereof. Although certain embodiments of the invention are specifically described herein, one of ordinary skill in the art will readily recognize that the same principles are equally applicable to, and can be employed in other apparatuses and methods. Before explaining the disclosed embodiments of the present invention in detail, it is to be understood that the invention is not limited in its application to the details of any particular embodiment shown. The terminology used herein is for the purpose of description and not of limitation. Further, although certain methods are described with reference to certain steps that are presented herein in certain order, in many instances, these steps may be performed in any order as may be appreciated by one skilled in the art, and the methods are not limited to the particular arrangement of steps disclosed herein.

As used herein and in the appended claims, the singular forms "a", "an", and "the" include plural references unless the context clearly dictates otherwise. The singular form of any class of the ingredients refer not only to one chemical species within that class, but also to a mixture of those chemical species; for example, the term "solvent" in the singular form, may refer to a mixture of compounds each of which is also a solvent. The terms "a" (or "an"), "one or more" and "at least one" can be used interchangeably herein. It is also to be noted that the terms "comprising", "including", and "having" can be used interchangeably.

The term "about" when referring to a number means ±3%. For example, the phrase "about 50 wt %" refers to a number between and including 48.500 and 51.500. The term "wt %" means percent by weight.

The phrase "nail polish," also sometimes referred to in literature as "nail enamel" or "nail varnish," is a lacquer that is suitable to be applied to fingernails or toenails to decorate or protect the nail plates. The terms "nail", and by extension "fingernail" and "toenail," refer to either a natural nail or artificial nail. The term "nail" also refers to a human nail, as well as to any toughened keratin at the end of a digit of a non-human animal.

Phrases "top coat nail polish formulation" and "top coat nail polish" refer to a nail polish that is particularly suitable by its chemical and physical properties as a top coat, but may be used for other purposes. The phrase "top coat" is typically the top-most nail polish layer applied to nails, covering a colored nail polish layer, or crackle coat layer, which may in turn cover a base nail polish layer.

The present invention relates to a copolymer of methyl methacrylate, methacrylic acid and an alkylacrylate, suitable for use in a top coat nail polish formulation. This type of copolymer is herein classified as a "secondary film forming polymer."

The term "copolymer" means a polymer comprising more than one species of monomer. The copolymer of the present invention consists of, or comprises essentially of, one or more linear chain copolymers. Examples of a copolymer include a statistical copolymer, a random copolymer, an alternating copolymer, a periodic copolymer, and a block copolymer. Under one embodiment of the present invention, the copolymer is a statistical copolymer or a random copolymer. The term "terpolymer" is a polymer comprising three species of monomer.

The definition of the term "acrylate" as referred to in the monomeric form, includes an ester, a salt, or a conjugate base of acrylic acid, with the formula $CH_2=CH-COO^-$. The definition of the term "acrylate" referred to in the polymeric form includes the repeating unit of an ester, a salt, or a conjugate base of acrylic acid, with the formula $-[CH_2-C(H)(COO^-)]-$.

The definition of the term "methacrylate" as referred to in the monomeric form includes an ester, a salt, or a conjugate base of methacrylic acid, with the formula $CH_2=C(CH_3)-COO^-$. The definition of the term "methacrylate" as referred to in the polymeric form includes an ester, a salt, or a conjugate base of methacrylic acid, with the formula —[CH$_2$=C(CH$_3$)—COO$^-$]—.

Methyl methacrylate ("MMA") is a composition consisting of, or comprising largely of, the compound of formula CH$_2$=C(CH$_3$)—COOCH$_3$. MMA may be prepared by any of the known synthetic routes, including condensation of acetone and hydrogen cyanide to produce cyanohydrins, which is hydrolyzed with sulfuric acid to yield methacrylamide ester, followed by a methanolysis. When referring to a portion of a copolymer, the term "methyl methacrylate" refers to the portion of the copolymer originated from the monomer methyl methacrylate, and has the structure —[CH$_2$—C(CH$_3$)(COOCH$_3$)]—.

Methacrylic acid ("MAA") is a composition consisting of, or comprising largely of, the compound of formula CH$_2$=C(CH$_3$)—COOH. When referring to a portion of a copolymer, the term "methacrylic acid" refers to the portion of the copolymer originated from the monomer methacrylic acid, and has the structure —[CH$_2$—C(CH$_3$)(COOH)]—.

Alkylacrylate is a composition consisting of, or comprising largely of, one or more compounds of formula CH$_2$=CH—COOR, wherein the moiety R is an alkyl group. When referring to a portion of a copolymer, the term "alkylacrylate" refers to the portion of the copolymer originated from the monomer methacrylic acid, and has the structure —CH$_2$—C(CH$_3$)(COOR)—. Specifically included in the definition of the term "alkylacrylate" is a mixture of two or more compounds each of which is also an alkylacrylate.

The phrase "alkyl group" relates to a linear or branched saturated hydrocarbon group, which is bound to the rest of the molecule by means of a single bond. The alkyl group may contain any number of carbons that would be appropriate for use in nail polish composition. The term "alkyl group", unless specifically referred to otherwise, may be a branched alkyl group, a linear alkyl group. The adjective form "alkyl" without a noun that it modifies following it means an "alkyl group"; likewise, the term "methyl" without a noun that it modifies following it means a "methyl group", etc.

[Preparation of the Copolymer]

One type of a copolymer of the present invention is prepared by a reaction of: (a) about 0.5 wt % to about 5 wt % of methacrylic acid; (b) about 25 wt % to about 45 wt % of at least one alkylacrylate, wherein alkylacrylate is CH$_2$=CH—C(O)—OR, wherein R is a branched C$_4$ to C$_{12}$ alkyl group; and (c) about 50 to about 74.5 wt % of methyl methacrylate. This copolymer comprises acrylate units that comprise branched alkyl groups.

This copolymer may be prepared by adding a mixture of methacrylic acid, alkyl acrylate and methyl methacrylate to a stirred solution of a solvent. At least one free radical polymerization initiator may be added to polymerization reaction. The ratio of the three monomers is selected to reflect the desired weight ratios of the units in the copolymer.

The copolymerization of methacrylic acid, alkyl acrylate and methyl methacrylate generally occurs at elevated temperatures. Such temperatures may be achieved in a reaction vessel operating at an ambient pressure. Alternatively, the temperatures needed to achieve polymerization to completeness are above the ambient boiling point of one or more solvents, and may be undertaken in a high pressure vessel. The temperatures at which copolymerization occurs may be between 50° C. and 150° C., or between 80° C. and 130° C., or between 100° C. and 120° C.

The length of the reaction time needed for the synthesis of the copolymer to completion depends on various factors, including the identity and ratios of the monomers, concentration of the monomer mixture, rate at which the monomer mixture is added to the reactant vessel, temperature of the reaction vessel, solvent selection, identity and loading levels of the initiator, pressure under which the reaction takes place, the size of the reactant vessel, and like. The length of reaction time may be between 1 minute and 12 hours, or between 10 minutes and 6 hours, or between 30 minutes and 2 hours.

The copolymerization of methacrylic acid, alkyl acrylate and methyl methacrylate is a free radical polymerization. The copolymerization may be carried out under ambient air conditions. At elevated temperatures, oxygen solubility in the solvent is appreciably reduced allowing for polymerization to occur. Further, because oxygen present in the air may act as a radical scavenger, thus partially or fully inhibiting the reaction, this synthesis for commercial purposes may be carried out under inert atmosphere or possibly in a vacuum. Examples of suitable inert atmosphere include nitrogen, oxygen-depleted air, and noble gases such as argon.

The solvent may be any substance which is liquid in the temperature range of about −10° C. to about 50° C., does not interfere with the energy source or catalyst used to dissociate the initiator to form free radicals, is inert to the reactants and product, and will not otherwise adversely affect the reaction. Additionally, because the copolymer is generally not isolated from the copolymer/solvent mixture and thus will also appear in the final top coat nail polish formulation, the solvent in which the polymerization occurs, the health effects of the solvent and regulatory restrictions on the use of the solvent must be considered.

Suitable solvents for solution polymerizations include but are not limited to (1) esters such as acetates or ethanoates, including methyl acetate, ethyl acetate, isopropyl acetate, ethylhexyl acetate and butyl acetate: (2) ketones such as methyl ethyl ketone, cyclohexanone and acetone; (3) alcohols such as methanol, ethanol, n-propanol, isopropanol, n-butanol, isobutanol, 2-butanol, tert-butanol, 2-ethylhexanol, and glycerol; (4) aliphatic and aromatic hydrocarbons; and (5) mixtures thereof. Particularly suitable are solvents selected from the group consisting of methyl acetate, ethyl acetate, isopropyl acetate, methyl ethyl ketone, acetone, methanol, ethanol, n-propanol, isopropanol, n-butanol, and mixtures thereof. Further, particularly suitable are solvents which are the same or are readily miscible with the solvents in the top coat nail polish formulation. Particularly preferred solvent is a mixture of solvents.

The amount of solvent is generally about 30 to about 80 percent by weight based on the total weight of the reactants and solvent. For example, the amount of solvent ranges from about 40 weight percent to about 65 weight percent, based upon the total weight of the reactants and solvent, to yield fast reaction times. Under one embodiment of the present invention, the amount of the solvent is about 50 weight percent.

The reactants used to prepare the copolymer are methyl methacrylate monomer, methacrylic acid monomer and alkylacrylate monomer. These may be used in preparation of the copolymer as received from a manufacturer of these monomers, or any of these monomers may be purified prior to use, in order to increase the effectiveness of the copolymer.

Suitable alkylacrylates for the preparation of the copolymer of the present invention have the structural formula $CH_2=CH-C(O)-OR$, wherein R is a branched $C_4$ to $C_{12}$ alkyl group.

Under another embodiment suitable alkylacrylates for the preparation of the copolymer of the present invention have the structural formula $CH_2=CH-C(O)-OR$, wherein R is a branched $C_4$ to $C_{10}$ alkyl group.

Under still another embodiment suitable alkylacrylates for the preparation of the copolymer of the present invention have the structural formula $CH_2=CH-C(O)-OR$, wherein R is a branched $C_6$ to $C_{10}$ alkyl group.

The branched $C_4$ to $C_{12}$ alkyl group is saturated acyclic hydrocarbon group that contains at least one or more carbons that is bound to 3 or 4 other carbons. The branching may occur anywhere on the alkyl group.

Examples of a branched alkyl group include: 1-methylpropyl: sec-butyl; 2-methylpropyl; iso-butyl; 1,1-dimethylethyl; tert-butyl; 1-methylbutyl; sec-pentyl; 2-methylbutyl; 3-methylbutyl; 1-ethylpropyl; 3-pentyl; 1,1-dimethylpropyl; tert-pentyl; 1,2-dimethylpropyl; 2,2-dimethylpropyl; neopentyl; 1-methylpentyl; 2-methylpentyl; 3-methylpentyl; 4-methylpentyl; iso-amyl; 1,1-dimethylbutyl; 1,2-dimethylbutyl; 1,3-dimethylbutyl; 2,2-dimethylbutyl; 2,3-dimethylbutyl; 3,3-dimethylbutyl; 1-ethylbutyl; 2-ethylbutyl; 1,1,2-trimethylpropyl; 1,2,2-trimethylpropyl; 1-ethyl-1-methylpropyl, 1-ethyl-2-methylpropyl; 1-methylhexyl; 2-methylhexyl; 3-methylhexyl; 4-methylhexyl; 5-methylhexyl; 1,1-dimethylpentyl; 1,2-dimethylpentyl; 1,3-dimethylpentyl; 1,4-dimethylpentyl; 2,2-dimethylpentyl; 2,3-dimethylpentyl; 2,4-dimethylpentyl; 3,3-dimethylpentyl; 3,4-dimethylpentyl; 4,4-dimethylpentyl; 1-ethylpentyl; 2-ethylpentyl; 3-ethylpentyl; 1,1,2-trimethylbutyl; 1,1,3-trimethylbutyl; 1,2,2-trimethylbutyl; 1,2,3-trimethylbutyl; 1,3,3-trimethylbutyl; 2,2,3-trimethylbutyl; 2,3,3-trimethylbutyl; 1-(methylethyl)butyl; 1-ethyl-1-methylbutyl; 1-ethyl-3-methylbutyl; 2-(methylethyl)butyl; 2-ethyl-1-methylbutyl; 2-ethyl-2-methylbutyl; 2-ethyl-3-methylbutyl; 1-propylbutyl; 2-propylbutyl; 1,1,2,2-tetramethylpropyl; 1-ethyl-1,2-dimethylpropyl; 1-ethyl-2,2-dimethylpropyl; 1-ethyl-1,2-dimethylpropyl; 1-methylheptyl; 2-methylheptyl; 3-methylheptyl; 4-methylheptyl; 5-methylheptyl; 6-methylheptyl; 1,1-dimethylhexyl; 1,2-dimethylhexyl; 1,3-dimethylhexyl; 1,4-dimethylhexyl; 1,5-dimethylhexyl; 2,2-dimethylhexyl; 2,3-dimethylhexyl; 2,4-dimethylhexyl; 2,5-dimethylhexyl; 3,3-dimethylhexyl; 3,4-dimethylhexyl; 3,5-dimethylhexyl; 4,4-dimethylhexyl; 4,5-dimethylhexyl; 5,5-dimethylhexyl; 1-ethylhexyl; 2-ethylhexyl; 3-ethylhexyl; 4-ethylhexyl; 1,1,2-trimethylpentyl; 1,1,3-trimethylpentyl; 1,1,4-trimethylpentyl; 1,2,2-trimethylpentyl; 1,2,3-trimethylpentyl; 1,2,4-trimethylpentyl; 1,3,3-trimethylpentyl; 1,3,4-trimethylpentyl; 1,4,4-trimethylpentyl; 2,2,3-trimethylpentyl; 2,2,4-trimethylpentyl; 2,3,3-trimethylpentyl; 2,3,4-trimethylpentyl; 2,4,4-trimethylpentyl; 3,3,4-trimethylpentyl; 3,4,4-trimethylpentyl; 1-ethyl-1-methylpentyl; 1-ethyl-2-methylpentyl; 1-ethyl-3-methylpentyl; 1-ethyl-4-methylpentyl; 2-ethyl-1-methylpentyl; 2-ethyl-2-methylpentyl; 2-ethyl-3-methylpentyl; 2-ethyl-4-methylpentyl; 3-ethyl-1-methylpentyl; 3-ethyl-2-methylpentyl; 3-ethyl-3-methylpentyl; 3-ethyl-4-methylpentyl; 1-propylpentyl; 2-propylpentyl; 1-(methylethyl)pentyl; 2-(methylethyl)pentyl; 3-(methylethyl)pentyl; 1,1,2,2-tetramethylbutyl; 1,1,2,3-tetramethylbutyl; 1,1,3,3-tetramethylbutyl; 1,2,2,3-tetramethylbutyl; 1,2,3,3-tetramethylbutyl; 2,2,3,3-tetramethylbutyl; 1-ethyl-1,2-dimethylbutyl; 1-ethyl-1,3-dimethylbutyl; 1-ethyl-2,2-dimethylbutyl; 1-ethyl-2,3-dimethylbutyl; 1-ethyl-3,3-dimethylbutyl; 2-ethyl-1,1-dimethylbutyl; 2-ethyl-1,2-dimethylbutyl; 2-ethyl-1,3-dimethylbutyl; 2-ethyl-2,3-dimethylbutyl; 2-ethyl-3,3-dimethylbutyl; 1,1-diethylbutyl; 1,2-diethylbutyl; 2,2-diethylbutyl; 1-methyl-1-propylbutyl; 2-methyl-1-propylbutyl; 3-methyl-1-propylbutyl; 1-methyl-1-(methylethyl)butyl; 2-methyl-1-(methylethyl)butyl; 3-methyl-1-(methylethyl)butyl; 1-methyl-2-(methylethyl)butyl; 2-methyl-2-(methylethyl)butyl; 3-methyl-2-(methylethyl)butyl; 1-(1,1-dimethylethyl)butyl; mixtures thereof; and like.

Further examples of branched alkyl groups include 8-methylnonyl, and 3,5,5-trimethylhexyl.

Under one embodiment the branched alkyl group is selected from the group consisting of iso-butyl, tert-butyl, 2-methylbutyl, 5-methylhexyl, 2-ethylhexyl, iso-octyl, 6-methylheptyl, 3,5,5-trimethylhexyl, 8-methylnonyl, and iso-decyl. Under another embodiment the branched alkyl group 2-ethylhexyl.

The alkylacrylate may be a mixture of different alkylacrylates, and thus the alkylacrylate in the copolymer may contain a mixture of branched alkyl groups.

Another type of copolymer of the present invention is prepared by a reaction of (a) about 0.5 to about 5 wt % of methacrylic acid; (b) about 25 to about 45 wt % of a mixture of at least one branched $C_4$ to $C_{12}$ alkyl acrylate and zero, one or more linear $C_3$ to $C_{16}$ alkyl acrylate; and (c) about 50 to about 74.5 wt % of methyl methacrylate. This copolymer comprises acrylate units that comprise one or more branched alkyl groups, and optionally one or more linear alkyl groups.

In this type of a copolymer of the present invention, the mixture of alkyl groups may be a mixture of branched alkyl groups, or a mixture of linear and branched alkyl groups.

Examples of linear alkyl chain include ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, and n-hexadecyl.

One example of this copolymer is a polymer comprising acrylate units that comprise two branched alkyl groups, such as 2-methylbutyl and 5-methylhexyl. Another example of this copolymer is a polymer comprising acrylate units that comprise one branched alkyl group and one linear alkyl group, such as 2-methylbutyl and n-hexyl. Yet another example of this copolymer is a polymer comprising acrylate units that comprise two branched alkyl groups and one linear alkyl group, such as 2-methylbutyl, 5-methylhexyl, and n-hexyl. Still another example of this copolymer is a polymer comprising acrylate units that comprise two branched alkyl groups and two linear alkyl groups, such as 2-methylbutyl, 5-methylhexyl, n-hexyl, and n-octyl.

To assist the polymerization of the methacrylic acid, alkyl acrylate, and methyl methacrylate monomers to form the copolymer of the present invention and in order to regulate the molecular weight of copolymer, a chain transfer agent may be added. Representative examples of chain transfer agents include mercaptans, such as octyl mercaptan, n-dodecyl mercaptan, tert-dodecyl mercaptan, n-hexadecyl mercaptan, n-tetradecyl mercaptan and t-tetradecyl mercaptan; xanthogen disulfides, such as dimethylxanthogen disulfide, diethylxanthogen disulfide and diisopropylxanthogen disulfide; thiuram disulfides, such as tetramethylthiuram disulfide, tetraethylthiuram disulfide and tetrabutylthiuram disulfide; halogenated hydrocarbons, such as carbon tetrachloride and ethylene bromide; hydrocarbons, such as pentaphenylethane; unsaturated cyclic hydrocarbon compounds, such as acrolein, methacrolein, allyl alcohol, 2-ethylhexyl thioglycolate, turbinolene, α-terpinene, γ-terpinene, dipentene, a-methylstyrene dimer (preferably containing at least 50 parts by weight of 2-4-diphenyl-4-methyl-1-pentene), 9,10-dihydroanthracene, 1,4-dihydronaphthalene, indene and 1,4-cyclohexadiene; and unsaturated heterocyclic compounds, such as xanthene and 2,5-dihydrofuran. These may be used either alone, or in combination. The chain transfer agent is used at a level from about 0.25 weight percent to 3 weight percent, preferably at a level of from 0.5 weight percent to 2 weight percent based on total weight of monomers.

Further, the polymerization of the monomers in the reaction mixture is undertaken in the presence of 0.001 to 1 wt % of one or more initiators. The one or more initiators may be thermal initiators or photoinitiators selected from, but not limited to, the carbonyl compounds such as benzoin, benzoin methyl ether, benzoin ethyl ether, benzoin propyl ether, benzoin-n-butyl ether, benzoin isobutyl ether, acetoin, butyroin, toluoin, benzil, benzophenone, para methoxybenzophenone, 2,2-diethoxyacetophenone, α,α-dimethoxy-α-phenylacetophenone, methylphenyl glyoxylate, ethyphenyl glyoxylate, 4,4'-bis-(dimethylaminobenzophenone), propiophenone, acetophenone, 1-hydroxycyclohexyl phenyl ketone, 2,2-diethoxyacetophenone, ethlphenylpyloxylate, phenanthraquinone, and 2-hydroxy-2-methyl-1-phenyl-propan-1-one; sulfur compounds such as tetramethylthiuram monosulfide and tetramethylthiuram disulfide; azo compounds such as azobisisobutyronitrile and azobis-2,4-dimethylvaleronitrile; and organic peroxide compounds such as benzoyl peroxide, dicumyl peroxide, methyl ethyl ketone peroxide; acetone peroxide, and di-tert-butyl peroxide, thioxanthone photoinitiators such as 7-chlorothioxanthone, 2,4-diethylthioxanthone and 2,4-diisopropylthioxanthone; and acylophosphine oxide photoinitiators. In addition to those above, commercially available proprietary free radical initiator compositions such as Irgacure (BASF, Ludwigshafen, DE), VAZO (Chemours, Wilmington, Del., US), Darocure (BASF), and like, can also be used to the same effect.

At the completion of the reaction, it is desirable to have the residual levels of any or all of the monomers to be less than 0.1 wt %. This can be accomplished by an optional step of adding an initiator chase. The initiator chase, also known in the polymerization art as initiator chase, or catalyst chase, or catalyst chaser, involves adding one or more initiators towards the end, or after the end, of the polymerization reaction, and extending the residency time further. The initiators employed in the initiator chase can be the same or different as the one used in conducting the polymerization. The chaser catalyst may be added to the reaction vessel neat, or in a solution comprising a solvent that is identical, similar, or miscible with the solvent in the reaction vessel.

After the completion of the reaction, including the optional initiator chase step, the mixture may be cooled and transferred to a storage vessel, or used further in the preparation of the nail polish top coat composition. The copolymer of the present invention is typically not isolated from solvent, and is used as a solution in any further preparation of the top coat nail polish formulation. However, in some cases the concentration of the copolymer in the solution may be increased by evaporating the solvent from the solution, or by performing solvent extractions.

The present invention is also directed to a solution comprising the copolymer described above. This solution for use in the preparation of a top coat nail polish formulation comprises (1) the copolymer prepared by a reaction of: (a) about 0.5 wt % to about 5 wt % of methacrylic acid; (b) about 25 wt % to about 45 wt % of at least one alkylacrylate of formula $CH_2=CH-C(O)-OR$, wherein R is a branched $C_4$ to $C_{12}$ alkyl group; and (c) about 50 wt % to about 74.5 wt % of methyl methacrylate; and (2) a solvent selected from the group consisting of methyl acetate, ethyl acetate, isopropyl acetate, methyl ethyl ketone, methanol, ethanol, n-propanol, isopropanol, n-butanol, and mixtures thereof.

This solution may contain 30 wt % to 70 wt % of the copolymer, with the balance being the solvent. The solvent is typically the solvent in which the synthesis of the copolymer occurred. Alternatively, in addition to the solvent that was used in the synthesis of the copolymer, the solvent may also include a supplementary solvent that is introduced after the completion of the synthesis of the copolymer. The supplementary solvent may be a solvent that may be particularly suitable for the preparation of the top coat nail polish formulation, but is not suitable for use in the synthesis of the copolymer.

The solution comprising the copolymer of the present invention has uses in many coating applications. One use for the solution comprising the copolymer is in the cosmetic industry: although particularly suitable for the preparation of top coat nail polish formulations, the solution may also be used in colored nail polish, base coat, or gel polish. Other uses of the solution comprising the copolymer include in vinyl topcoating, metal coating, steel coating, marine/intermodal container paints, non-ferrous metal coating, plastic coating, masonry coating, road marker paints, flexographic inks, rotogravure inks, screen inks, roll leaf for hot stamping, toners, binders, temporary binders, decals, construction bolt cement, PVC pipe cement, staple cement, decoupage, wall covering, artistic media, reactive coatings, self-leveling flooring, and like.

The present invention is also directed to a top coat nail polish composition comprising a top coat component that is useful in the manicure and pedicure arts. The top coat component comprises: (a) about 5 wt % to about 30 wt % primary film-forming polymer comprises at least one polymer selected from the group consisting of cellulose acetate, cellulose acetate propionate, cellulose acetate butyrate, ethyl cellulose, vinyl polymers, nitrocellulose, and mixtures thereof; (b) about 2 wt % to about 20 wt % secondary film-forming polymer; (c) about 1 wt % to about 5 wt % of at least one plasticizer; and (d) about 50 wt % to about 80 wt % solvent; said wt % of components (a) to (d) are based on the total weight of the component; and wherein the secondary film-forming polymer comprises a copolymer prepared by a reaction of: (i) about 0.5 to about 5 wt % of methacrylic acid; (ii) about 25 to about 45 wt % of $CH_2=CH-C(O)-OR$, wherein R is a branched $C_4$ to $C_{12}$ alkyl group; and (iii) about 50 to about 74.5 wt % of methyl methacrylate; said wt % of components (i) to (iii) are based on the total weight of the copolymer.

The reaction of ingredients (a) primary film-forming polymer, (b) secondary film component, (c) plasticizer, and (d) solvent, as described above, form a top coat component for use in preparing a top coat nail polish composition. Under one embodiment of the present invention no additional ingredients are necessary to complete formulating the top coat nail polish composition, thus the top coat nail polish composition is the top coat component. Under another embodiment the top coat nail polish composition consists of the top coat component, any of additional ingredients, such as reactive species compatible with film-forming polymers, free radical source, clarifiers, fragrance, natural extracts, hydrolyzed conchiolin protein, *lilium candidum* bulb extract, retinyl palmitate, *simmondsia chinensis* (jojoba) seed oil, tocopherol, *arachis hypogaea* (peanut) oil, and like.

In the manicure and pedicure arts, the top coat nail polish composition is typically clear and colorless, and the dried top coat is also typically clear and colorless, thus pigments or colorants are generally not added. However, for selected special purpose top coat nail polishes, the top coat nail polish composition of the present invention may also include pigments, colorants, or brighteners.

The top coat nail polish composition is a lacquer that may be applied to fingernails or toenails. Of a particular use of the top coat nail polish composition of the present invention is the formation of the final layer of a manicure. The top coat nail polish formulation is applied after applying a colored nail polish. When applied and dried, the top coat forms a hardened barrier for the nail, which gives nails a glossy shine, prevents chipping and scratching of the colored layer. One of the advantages of the top coat formed by the application of the clear nail polish composition of the present invention is the lack of or low amounts of haze.

The definition of the phrase "top coat nail polish formulation" also includes any of compositions which are used for other purposes than in manicure and pedicure arts that provide the desired properties of the top coat nail polish composition. Top coat nail polish formulations are often used by the end user in an off-label manner, typically referred to colloquially as "life hacks", "everyday hacks", or "household hacks". Such "hacks" refer to any tricks, shortcut, skill, or novelty method that increases productivity and efficiency, in all walks of life. Top coat nail polish formulation is particularly susceptible for use in a hack, because it is well known to a large percentage of people, is common in most households, and readily usable, and most people do not have other similar types of products readily available in their household.

For example, the top coat nail polish composition of the present invention may be used to coat labels to create smudge-proof and weather-resistant labels for identification of seedlings in a garden, seal postal envelopes, tread a needle, prevent costume jewelry from tarnishing, keeping laces and rope from unraveling, tightening loose screws, rustproof bathroom metal containers, use as a topical skin treatment for minor cuts and sores, repair scratches to automobile paint, repair windshield cracks, waterproof matches, repair scratches and splinters in furniture, coat belt buckles, remove warts, seal pet collar tags, secure treads on buttons on clothing, seal selected holes in salt shakers, and like. Because the top coat formed seals, protects and adds gloss, the top coat nail polish composition of the present is envisioned to work better for the uses outside of the manicure and pedicure arts, compared to other clear nail polish formulations or clear base coats.

The amounts of primary film-forming polymer and secondary film-forming polymer are selected to produce a dried coating thickness of about 0.001 inches to about 0.005 inches (about 25 µm to 125 µm), preferably about 0.002 inches to 0.003 inches (50 µm to 75 µm).

The primary film-forming polymers provide body and viscosity functionality in the top coat nail polish composition. Primary film-formers useful in the top coat component are selected for their hardness, toughness, resistance to abrasion and ability to release solvent rapidly. Primary film-forming polymers useful in the top coat component include cellulose acetate, cellulose acetate propionate, cellulose acetate butyrate, ethyl cellulose, vinyl polymers, nitrocellulose, and mixtures thereof.

Nitrocellulose provides an unusual combination of properties of toughness, durability, solubility and solvent release, and is one of the preferred primary film-forming polymers.

Examples of nitrocellulose are the so called nitrocellulose RS ⅛ sec. and ¼ sec.; nitrocellulose RS ½ sec.; and nitrocellulose RS 5-6 sec. and 60-80 sec. The term "RS" refers to the class of nitrocellulose with a nitrogen content of about 11.2 to about 12.8% with solubility in esters, ketones and glycol ethers manufactured by Dow (Wilmington, Del., US). The terms ⅛ sec., sec., ¼ sec., 5-6 sec., etc. represent viscosity and refer to the time it takes for a ball to fall to a given depth in the material. Other useful nitrocelluloses include A-grade nitrocellulose (nitrogen content 10.7% to 11.3%), AM-grade nitrocellulose (nitrogen content 11.3% to 11.8%), and E-grade nitrocellulose (nitrogen content 11.8% to 12.3%). Nitrocellulose is typically supplied in concentrations between 40% to 70% concentrations, wet with an alcohol or acetate solvent.

In addition to cellulose acetate, cellulose acetate propionate, cellulose acetate butyrate, ethyl cellulose, vinyl polymers, nitrocellulose, and mixtures thereof, the primary film-forming polymer may comprise additional polymer species that function as primary film-forming polymers.

The phrase "primary film-forming polymer" under one embodiment refers to a single polymer species. Under another embodiment, the phrase "primary film-forming polymer" refers to a mixture of polymer species.

The primary film-forming polymer is present in the top coat composition in an amount ranging from about 5% to about 30% by weight of the composition, and more preferably in the range of about 10% to about 15% by weight of the composition.

The secondary film-forming component in the top coat composition necessarily comprises the copolymer of the present application described above. Under one embodiment, the copolymer prepared as described above is the only secondary film-forming component present. Under another embodiment, the secondary film-forming component may also comprise additional secondary film formers.

Additional secondary film formers useful in the top coat component are chosen on the basis of their ability to build film and to enhance the lack of haze, gloss and adhesion of the applied coating. Useful additional secondary film formers include drying and nondrying alkyd resin, vinyl polymers such as polyvinyl acetate and polyvinyl butyral; arylsulfonamide-formaldehyde resins, for example toluene sulfonamide-formaldehyde resin, polyether urethanes such as polyurethane resins; polyester resins from mixtures of 2,2,4-trimethyl-1,3-pentanediol, isophthalic acid-85, and trimellitic anhydride.

Plasticizers employed in the top coat composition are chosen to impart flexibility to the hardened coating. The properties of the top coat composition are improved when blended with plasticizers, if these substances can embed themselves between the chains of polymers to increase the free volume between the polymer chains, thereby lowering the glass transition temperature, increasing flexibility, effecting hardness and/or improving durability. The choice of plasticizer may vary as a function of the effect on viscosity of the top coat nail polish formulation, effect on the drying rate, the amount needed to meet flexibility requirements, the volatility of the plasticizer, as well as compatibility with the other components of the top coat nail polish formulation.

Commonly used plasticizers are from the chemical classes of sebacates, adipates, terephthalates, dibenzoates, gluterates, phthalates, azelates, glycols, polyethers and polycarboxylic acids with linear chain or branched aliphatic alcohols and blends of these. These compounds are selected because of low toxicity, compatibility with the nail plate, formula composition and with the final polymerized material. The most preferred examples have low volatility and do not quickly escape from the resulting synthetic polymer via migration and evaporation.

Plasticizers which may be used in the top coat composition include dibutyl phthalate, camphor, butyl phthalate, butyl glycolate, triphenyl phosphate, tricresyl phosphate, diamylphthalate, dibutyl phthalate, diethyl phthalate, dibutoxy ethyl phthalate, dioctyl phthalate, castor oil, benzyl benzoate, glyceryl tribenzoate, tributyl phosphate, triphenyl phosphate, sucrose benzoate, butyl acetyl ricinoleate, acetyl tributyl citrate, butyl stearate, triethyl citrate, dibutyl tartrate, diamyl phthalate, propylene glycol adipate, mixtures thereof, and other common plastisizers used in acrylic and nitrocellulose nail polish formulations for flexibility and chip resistance.

The plasticizer is employed in the top coat composition in an amount of about 1 wt % to about 5 wt %. Alternatively, the plasticizer is employed in the top coat composition in an amount of about 1 wt % to about 3 wt %.

The solvent for use in preparation of the top coat composition may be any substance which is liquid in the temperature range of about −10° C. to about 50° C., dissolves or suspends the components of the formulation, and yields desirable properties associated with nail art, such as lack of haze and drying time. The health effects of the solvent and legislative restrictions on the use of the solvent in nail care formulations must be considered.

Suitable solvents for use in preparation of the top coat composition include alkanes having 4 to 10 carbon atoms per molecule, aliphatic esters having 3 to 10 carbon atoms per molecule, alkanols having 2 to 10 carbon atoms per molecule, e.g., n-butane, isobutane, n-pentane, isopentane, hexane, heptane, isoheptane, octane, 3,3-dimethyl hexane, 3-ethyl hexane, nonane, 2,2,3-trimethyl hexane, 2-methyl octane, 3-ethyl-2-methyl hexane, 2,3-dimethyl octane, decane, methyl propionate, methyl acetate, ethyl acetate, n-propyl acetate, n-butyl acetate, isobutyl acetate, sec-butyl acetate, tert-butyl acetate, 1,1-dimethyl butyl acetate, n-propyl formate, ethyl propionate, hexyl acetate, 3-ethyl-3-pentyl acetate, octyl acetate, 2-ethyl hexyl acetate, ethanol, n-propanol, isopropanol, n-butanol, n-pentanol, n-hexanol, n-heptanol, 3-methyl 3-hexanol, 2-ethyl 3-hexanol, n-octanol, n-decanol, and mixtures of any two or more thereof. Under one embodiment the preferred aliphatic esters are the acyclic hydrocarbyl esters having 3 to 6 carbon atoms per molecule, and the preferred alkanols are those having 3 to 6 carbon atoms per molecule.

Further suitable solvents use in preparation of the top coat composition include cycloalkanes having 4 to 10 carbon atoms per molecule, cycloaliphatic esters having 4 to 10 carbon atoms per molecule, cycloalkanols having 4 to 10 carbon atoms per molecule, e.g., cyclobutane, cyclopentane, methyl cyclobutane, cyclohexane, ethyl cyclobutane, methyl cyclopentane, ethyl cyclopentane, propyl cyclopentane, 1,1,2-trimethyl cyclopentane, 1,1-dimethyl cyclohexane, 1,2-dimethyl cyclohexane, 1,3-dimethyl cyclohexane, 1,4-dimethyl cyclohexane, ethyl cyclohexane, propyl cyclohexane, isopropyl cyclohexane, 1,1,3-trimethyl cyclohexane, 1-methyl-4-ethyl cyclohexane, n-butyl cyclohexane, isobutyl cyclohexane, cyclobutanol, cyclobutylcarbinol, cyclopentanol, naphthenes, and mixtures of any two or more thereof.

Additionally, suitable solvents are selected from the group consisting of methyl acetate, ethyl acetate, isopropyl acetate, methyl ethyl ketone, acetone, methanol, ethanol, n-propanol, isopropanol, n-butanol, and mixtures thereof.

High-boiling point solvents such as heptane may be added to the solvent system, but care must be taken to limit the use of such solvents to sufficiently low levels to avoid unnecessarily increasing the drying time.

The amount of solvent is generally about 50 to about 85 percent by weight based on the total weight of the top coat composition. This value includes the solvents that are added to the top coat component directly, the solvent in which the copolymer was formed, solvents that are included with the first film-forming component, and solvents that are included with any additional second film-forming components.

One of the advantage of the present formulation over prior art is the reduction of haze in a typical nail polish formulation.

The causes behind the formation of haze is not well understood, but it is hypothesized that microstructures in coating films such as dried nail polish can cause a milky appearance, or haze. This effect is often caused by specific parameters in the formulation of the liquid nail polish, production processes, degree of dispersion, or application process. For example, the haze formation may be due to an incompatibility between acrylic/methacrylic polymer and nitrocellulose. Further, the formation of haze may be influenced by the hydrophilic solvent mixture in the composition. One conjecture relates the haze to the overall hydrophobicity of the copolymer.

Haze can be evaluated by measuring the diffuse scattered light. Haze in coating films such as dried nail polish is often designated "reflection haze" because in plastics there is encountered a near-forward scattering in transmission that is designated as transmission haze. Further, the ASTM standard E284-13b entitled Terminology of Appearance defines "haze" in reflection as percent of reflected light scattered by a specimen having a glossy surface so that its direction deviates more than a specified angle from the direction of specular reflection.

The haze measurement of any one of the nail polish formulation described above may be evaluated by any of techniques commonly used in the cosmetic industry. The haze may be measured using a goniophotometer. The haze properties of the coating film using a 60° angle may also be measured using a reflection haze meter, such that available from BYK Gardner (Geretsried, DE). The haze measurement may be obtained by any of appropriate standards such as ISO 13803:2014, ASTM E430-11 and DIN 67530. Due to the variance in surface roughness of dried nail polish, the techniques to measure the haze may need to be adapted from the aforementioned standards. The haze may also be determined by a semi-quantitative judgment by a well trained or well experienced cosmetic formulator.

Samples for haze measurement evaluation may be prepared in accordance with ASTM standard G 147-09 entitled Standard Practice for Conditioning and Handling of Non-Metallic Materials for Natural and Artificial Weathering Tests, or a similar technique. The samples were based upon a dried 3 mil film drawn on a substrate obtained from The Leneta Company (Mahwah, N.J., US)

There appear to be four factors associated with the copolymer composition that govern the haze characteristics in the typical dried nail formulations comprising the copolymer.

The first factor associated with the copolymer composition that determines the haze characteristics in the typical dried nail formulations comprising the copolymer is the presence of methacrylic acid. Methacrylic acid monomer is necessary in the preparation of the copolymer of the present invention. Without the methacrylic acid monomer, the dried coating film has a strong haze present, even if the other factors are chosen appropriately. The loading level of the methacrylic acid monomer is about 0.5 wt % to about 5 wt % with respect to the total amount of monomers. Under one embodiment the loading level of the methacrylic acid monomer is about 1 wt % to about 2 wt % with respect to the total amount of monomer. Under another embodiment, the loading level of the methacrylic acid monomer is about 0.8 to 1.8 wt % with respect to the total amount of monomer.

The second factor associated with the copolymer composition that determines the haze characteristics in the typical dried nail formulations comprising the copolymer is the weight ratio of methyl methacrylate to alkyl acrylate. The haze is reduced or eliminated when the weight ratio of methyl methacrylate to alkyl acrylate is between about 1:1 and 3:1. A strong haze is present if the majority of the polymer is alkyl acrylate or there is too little of the alky acrylate.

Under one embodiment of the present invention, the weight ratios of the methacrylic acid, alkyl acrylate, and methyl methacrylate is 0.5-5 wt %:25-45 wt %:53.5-74 wt %. The weight ratios add up to 100 wt %.

In order to eliminate or minimize haze, judicious selection of the weight percentages is generally required. This is because haze depends on several factors, including process parameters, commercial source of the top coat components such as the primary film-forming polymer. Therefore, the optimal weight percentages of methacrylic acid, alkyl acrylate, and methyl methacrylate for one top coat nail polish formulation may not be the optimal weight percentages of similar top coat nail polish formulation.

Under one embodiment the weight percentages of the methacrylic acid, alkyl acrylate, and methyl methacrylate is about 1 wt % to about 2 wt %:about 29 wt % to about 33 wt %:about 65 wt % to about 70 wt %. Under another embodiment the weight percentages of the methacrylic acid, alkyl acrylate, and methyl methacrylate is about 1 wt % to about 2 wt %:about 33 wt % to about 37 wt %:about 61 wt % to about 66 wt %. Under yet another embodiment the weight percentages of the methacrylic acid, alkyl acrylate, and methyl methacrylate is about 1 wt % to about 2 wt %:about 37 wt % to about 41 wt %:about 57 to about 62 wt %. In all of the foregoing, the weight ratios add up to 100 wt %.

It is understood that although the copolymer of the present application consists primarily of the terpolymer of methacrylic acid, alkyl acrylate, and methyl methacrylate, the copolymer of the present may also comprise additional monomeric units; such additional monomeric units may be present due to impurities in the starting material or due to addition of monomers that have no effect on the haze formation. In copolymers where additional monomers are present, the above weight percentages of the methacrylic acid, alkyl acrylate, and methyl methacrylate are with respect to the total amount of methacrylic acid, alkyl acrylate, and methyl methacrylate.

The third factor associated with the copolymer composition that determines the haze characteristics in the typical dried nail formulations comprising the copolymer is the number of carbon atoms in the alkyl group in the alkyl acrylate. Under one embodiment of the present invention, the average number of carbons in the alkyl group in alkylacrylate is 4 to 12. Under another embodiment, the haze is reduced or eliminated when the average number of carbons in the alkyl group in the alkylacrylate is 4 to 10.

Under one embodiment of the present invention, the alkyl group contains 4 to 12 carbon atoms. Examples of alkyl groups include butyl, pentyl, hexyl, heptyl, octyl, nonyl, decyl, undecyl, dodecyl, isomers thereof, and mixtures thereof. The alkyl groups branched.

The alkylacrylate may be a single species, such as, for example octylacrylate. Additionally, alkylacrylate may be a mixture of two or more compounds each of which is also an alkylacrylate. Therefore, one example of an alkylacrylate wherein the average number of carbons in the alkyl group equals 8 is octylacrylate; a second example of an alkylacrylate wherein the average number of carbons in the alkyl group equals 8 is a 1:1 (molar ratio) mixture of heptylacrylate and nonylacrylate; a third example of an alkylacrylate wherein the average number of carbons in the alkyl group equals 7 is a 1:2:1 (molar ratio) mixture of heptylacrylate, octylacrylate and nonylacrylate.

The fourth factor associated with the copolymer composition that determines the haze characteristics in the typical dried nail formulations comprising the copolymer is the branching of the alkyl group of the alkylacrylate.

The alkylacrylate may be a mixture of different alkylacrylates, and thus the alkylacrylate in the copolymer may contain a mixture of alkyl groups. This mixture of alkyl groups may be a mixture of branched alkyl groups, or a mixture of linear and branched alkyl groups.

Although not bound by any theory, the results suggest that both polymer packing (branched versus linear alkyl groups on backbone) and polymer hydrophobic/hydrophilic balance may impact the formation of microstructures that cause the haze.

Alternatively, the minimization of haze may be due to a mitigation of incompatibility between the copolymer of the present invention and nitrocellulose, and/or the solvent effect.

EXPERIMENTAL

Materials.

Methyl methacrylate ($CH_2=C(CH_3)-COOCH_3$, "MMA", 99%), butyl acrylate ($CH_3-COO-(CH_2)_3CH_3$, "BA", 99%), methacrylic acid ($CH_2=C(CH_3)-COOH$, "MAA", 99%), 2-ethylhexyl acrylate ($CH_2=C(CH_3)-COO-CH_2-CH(CH_2CH_3)-(CH_2)_3CH_3$, "EHA", 99%), hexyl acrylate ($CH_2=C(CH_3)-COO-(CH_2)_5CH_3$, "HA", 98%), and lauryl acrylate ($CH_2=C(CH_3)-COO-(CH_2)_5CH_3$, "LA", 90%) were obtained from Sigma-Aldrich (Merck KGaA, Darmstadt, Germany). 2,2'-azodi(2-methylbutyronitrile) was obtained from DuPont as Vazo 67. Cellulose acetate butyrate, plasticizers, acetate and alcohol solvents, and nitrocellulose were obtained from commercial sources.

Copolymer Preparation.

A modified full factorial 2-factor 3×4 experiment was designed. The loading level factor had three levels (15, 31, and 50 wt % of alkyl acrylate), and the alkyl chain length factor had four levels ($C_4$, $C_6$, $C_8$, $C_{12}$). Additional runs (Experiment Nos. 8, 10) were performed for interstitial values of 20 and 40 wt % for 2-ethylhexylacrylate. Further additional runs (Experiment Nos. 15 and 16) were made to investigate the effect of the methacrylic acid loading. The ingredients and their loading levels of each of the sixteen Examples are listed below in Table An exemplary copolymer comprising 1.3 wt % methacrylic acid monomer, 31.0 wt % hexyl acrylate monomer, and 67.7 wt % methyl methacrylate monomer was prepared in a three neck 500 mL reaction vessel equipped with a nitrogen/vacuum port, a stirrer, and a reflux condenser. The atmosphere in the reaction vessel was replaced with nitrogen, 30 g of butyl acetate was added, heated up to 110° C.

While the contents of the reaction vessels were stirred, a mixture of 82.30 g of methyl methacrylate, 37.69 g of hexyl acrylate, 1.58 g of methyl methacrylate, 10.0 g of butyl acetate, 0.50 g of 2,2'-azodi(2-methylbutyronitrile), and 1.06 g of n-dodecyl mercaptan were added over a period of 2 hours at 110° C. After a hold time of 20 minutes at 110° C., the reaction vessel was cooled to 105° C., and additional 0.50 g of 2,2'-azodi(2-methylbutyronitrile) in 10.0 g of butyl acetate was added. The resulting mixture was held at 100 to 105° C. for additional 45 minutes, after which 70.0 g of butyl acetate was added. The mixture was stirred at the elevated temperature until homogenous, after which the mixture was cooled below 60° C., and transferred to a storage vessel.

This preparation yields a solution containing 50% copolymer in butyl acetate solvent. The copolymer obtained comprises a mixture of methacrylic acid, 2-ethylhexyl acrylate, and methyl methacrylate units in about a 1.3:31:67.7 weight percent.

The weight-average (Mw) and number-average (Mn) molar masses were determined by liquid chromatography by gel permeation. The weight-average mass (Mw) of the prepared copolymer was about 30,000 g/mol, and the number-average mass (Mn) of the copolymer was about 12,000 g/mol, giving a polydispersity index I of about 2.5.

Additional fifteen exemplary copolymers were prepared in a similar manner, with the appropriate monomers, and correcting for reactivity.

Top Coat Nail Polish Formulation.

For each of the synthesized copolymers, a top coat nail polish formulation comprising 5 wt % of the copolymer was prepared. The ingredients and their weight percentages are listed in Table 1.

TABLE 1

Top Coat Nail Polish Test Formulation comprising the copolymer of the present invention

| Ingredients | Wt % |
| --- | --- |
| Acetate Solvent | 62.3 |
| Alcohol Solvent | 12.3 |
| Nitrocellulose (net) | 10.0 |
| Cellulose acetate butyrate | 7.4 |
| Plasticizers | 3.0 |
| Copolymer (net) | 5.0 |
| | 100.0 |

The copolymer/butyl acetate mixture was used as prepared above. The weight percentage of the copolymer/butyl acetate mixture was 10.0%, which means that the weight percentage of the copolymer alone was 5.0% with respect to the overall top coat nail polish formulation.

Likewise, the weight percent of nitrocellulose listed in Table 1 is net of the solvent. The weight of the solvent used to suspend nitrocellulose is included in the weight percent of solvents listed in the table.

The procedure to prepare the top coat nail polish formulation for each of the 16 test formulations is as follows. Acetate and alcohol solvents were introduced into a mixing vessel, and solution/suspension of nitrocellulose was added. The mixture was stirred at about 50° C. until homogeneity was achieved. Cellulose acetate butyrate was added, followed by the addition of the above-prepared copolymer, and mixture was stirred to obtain a homogenous mixture.

Haze Evaluation.

Each of the top coat nail polish formulations described above was evaluated for haze of the formed dry coat. For each of the top coat nail polish formulations comprising the copolymers of Examples 1 to 16, a 1.0 mL bead of the formulation was placed onto a Leneta brushout card (Leneta Company). The bead was spread with a draw down bar (Leneta Company) to obtain an about 15 mil (about 400 µm) thickness of liquid film of the top coat nail polish formulation. The liquid film was left to dry overnight to form a dried top coat nail polish film. Each of the dried top coat nail polish films were semi-quantitatively evaluated for haze: "strong haze", "light haze", and "no haze".

The results of the haze evaluations of each of the dried top coat nail polish films comprising the copolymer are shown in Table 2, wherein MMA is methyl methacrylate, BA is butyl acrylate, MAA is methacrylic acid, EHA is 2-ethylhexyl acrylate, HA is hexyl acrylate, and LA is lauryl acrylate.

TABLE 2

Haze Evaluations of Dried Top Coat Nail Polish Films Comprising Copolymer

| Example # | Copolymer Composition (wt % of monomers) | Haze Result |
| --- | --- | --- |
| 1 | 25.0 BA/73.7 MMA/1.3 MAA | Light Haze |
| 2 | 37.5 BA/61.2 MMA/1.3 MAA | Light Haze |
| 3 | 50.0 BA/48.7 MMA/1.3 MAA | Strong Haze |
| 4 | 15.0 HA/83.7 MMA/1.3 MAA | Strong Haze |
| 5 | 31.0 HA/67.7 MMA/1.3 MAA | Light Haze |
| 6 | 50.0 HA/48.7 MMA/1.3 MAA | Strong Haze |
| 7 | 15.0 FHA/83.7 MMA/1.3 MAA | Strong Haze |
| 8 | 20.0 EHA/78.7 MMA/1.3 MAA | Strong Haze |
| 9 | 31.0 EHA/67.7 MMA/1.3 MAA | No Haze |
| 10 | 40.0 EHA/58.7 MMA/1.3 MAA | No Haze |
| 11 | 50,0 EHA/48.7 MMA/1.3 MAA | Strong Haze |
| 12 | 15.0 LA/83.7 MMA/1.3 MAA | Strong Haze |
| 13 | 31.0 LA/67.7 MMA/1.3 MAA | Strong Haze |
| 14 | 50,0 LA/48.7 MMA/1.3 MAA | Strong Haze |
| 15 | 31.0 BA/69.0 MMA | Strong Haze |
| 16 | 31.0 EHA/69.0 MMA | Strong Haze |

Based partially on the data above, it appears that the relative wt % of monomers, length of the alkyl group, branching of the alkyl group, and presence of methyl methacrylate all have a positive effect on the clarification of haze in the dried top coat nail polish film.

While the present invention has been described with reference to several embodiments, which embodiments have been set forth in considerable detail for the purposes of making a complete disclosure of the invention, such embodiments are merely exemplary and are not intended to be limiting or represent an exhaustive enumeration of all aspects of the invention. The scope of the invention is to be determined from the claims appended hereto. Further, it will be apparent to those of skill in the art that numerous changes may be made in such details without departing from the spirit and the principles of the invention.

What is claimed is:

1. A top coat nail polish formulation comprising a top coat composition comprising:
   (a) about 5 wt % to about 30 wt % primary film-forming polymer comprises at least one polymer selected from the group consisting of cellulose acetate, cellulose acetate propionate, cellulose acetate butyrate, ethyl cellulose, vinyl polymers, nitrocellulose, and mixtures thereof;

(b) about 2 wt % to about 20 wt % secondary film-forming polymer, (c) about 1 wt % to about 5 wt % of at least one plasticizer; and (d) about 50 wt % to about 85 wt % solvent;

said wt % of components (a) to (d) are based on the total weight of the component; and wherein the secondary film-forming polymer comprises a copolymer prepared by a reaction of:

(i) about 0.5 wt % to about 5 wt % of methacrylic acid;

(ii) about 25 wt % to about 45 wt % of at least one alkylacrylate of formula $CH_2=CH-C(O)-OR$, wherein R is a branched $C_4$ to $C_{12}$ alkyl group; and (iii) about 50 wt % to about 74.5 wt % of methyl methacrylate;

said wt % of components (i) to (iii) are based on the total weight of the copolymer; and wherein the nail polish formulation, once dried, has low or no haze.

2. The top coat nail polish formulation of claim 1, wherein the secondary film-forming polymer comprises the copolymer prepared by a reaction of:

(i) about 1 wt % to about 2 wt % of methacrylic acid;

(ii) about 29 wt/o to about 33 wt % of at least one alkylacrylate of formula $CH_2=CH-C(O)-OR$, wherein R is a branched $C_6$ to $C_{10}$ alkyl group; and (iii) about 65 wt % to about 70 wt % of methyl methacrylate.

3. The top coat nail polish formulation of claim 1, wherein the secondary film-forming polymer comprises the copolymer prepared by a reaction of:

(i) about 1 wt % to about 2 wt % of methacrylic acid;

(ii) about 33 wt % to about 37 wt % of at least one alkylacrylate of formula $CH_2=CH-C(O)-OR$, wherein R is a branched $C_6$ to $C_{10}$ alkyl group; and (iii) about 61 wt % to about 66 wt % of methyl methacrylate.

4. The top coat nail polish formulation of claim 1, wherein the secondary film-forming polymer comprises the copolymer prepared by a reaction of:

(i) about 1 wt % to about 2 wt % of methacrylic acid;

(ii) about 37 wt % to about 41 wt % of at least one alkylacrylate of formula $CH_2=CH-C(O)-OR$, wherein R is a branched $C_6$ to $C_{10}$ alkyl group; and (iii) about 57 wt % to about 62 wt % of methyl methacrylate.

5. The top coat nail polish formulation of claim 1, wherein R is selected from the group consisting of iso-butyl, tert-butyl, 2-methylbutyl, 5-methylhexyl, 2-ethylhexyl, isooctyl, 6-methylheptyl, 3,5,5-trimethylhexyl, 8-methylnonyl, and isodecyl.

6. The top coat nail polish formulation of claim 1, wherein R is 2-ethylhexyl.

7. The top coat nail polish formulation of claim 1, wherein the secondary film-forming polymer comprises the copolymer prepared by a reaction of:

(i) about 1 wt % to about 2 wt % of methacrylic acid;

(ii) about 25 wt % to about 45 wt % of at least one alkylacrylate of formula $CH_2=CH-C(O)-OR$, wherein R is a branched $C_4$ to $C_{12}$ alkyl group, and up to 15 wt % of at least one alkylacrylate of formula $CH_2=CH-C(O)-OR$, wherein R is a linear $C_3$ to $C_{16}$ alkyl group; and (iii) about 50 wt % to about 74 wt % of methyl methacrylate.

8. The top coat nail polish formulation of claim 2, wherein R is selected from the group consisting of iso-butyl, tert-butyl, 2-methylbutyl, 5-methylhexyl, 2-ethylhexyl, isooctyl, 6-methylheptyl, 3,5,5-trimethylhexyl, 8-methylnonyl, and isodecyl.

9. The top coat nail polish formulation of claim 3, wherein R is selected from the group consisting of iso-butyl, tert-butyl, 2-methylbutyl, 5-methylhexyl, 2-ethylhexyl, isooctyl, 6-methylheptyl, 3,5,5-trimethylhexyl, 8-methylnonyl, and isodecyl.

10. The top coat nail polish formulation of claim 4, wherein R is selected from the group consisting of iso-butyl, tert-butyl, 2-methylbutyl, 5-methylhexyl, 2-ethylhexyl, isooctyl, 6-methylheptyl, 3,5,5-trimethylhexyl, 8-methylnonyl, and isodecyl.

\* \* \* \* \*

UNITED STATES PATENT AND TRADEMARK OFFICE
CERTIFICATE OF CORRECTION

| | | |
|---|---|---|
| PATENT NO. | : 9,603,786 B1 | Page 1 of 1 |
| APPLICATION NO. | : 15/004432 | |
| DATED | : March 28, 2017 | |
| INVENTOR(S) | : Stephen Crescimanno | |

It is certified that error appears in the above-identified patent and that said Letters Patent is hereby corrected as shown below:

In the Claims
At Column 25, Line 24:
"(ii) about 29 w/o to about 33 wt % of at least one"
Should read:
-- (ii) about 29 wt % to about 33 wt % of at least one --.

Signed and Sealed this
First Day of August, 2017

Joseph Matal
*Performing the Functions and Duties of the*
*Under Secretary of Commerce for Intellectual Property and*
*Director of the United States Patent and Trademark Office*